United States Patent [19]

Nakagawa et al.

[11] Patent Number: 4,988,687

[45] Date of Patent: Jan. 29, 1991

[54] CEPHALOSPORIN DERIVATIVES, AND ANTIBACTERIAL AGENTS

[75] Inventors: Susumu Nakagawa; Ryuji Mitomo; Ryosuke Ushijima, all of Okazaki, Japan

[73] Assignee: Banyu Pharmaceutical Company, Ltd., Tokyo, Japan

[21] Appl. No.: 401,747

[22] Filed: Sep. 1, 1989

Related U.S. Application Data

[63] Continuation of Ser. No. 28,576, Mar. 20, 1987.

[30] Foreign Application Priority Data

Mar. 20, 1986 [JP] Japan ................................. 60-500

[51] Int. Cl.$^5$ .................. C07D 501/36; A61K 31/545
[52] U.S. Cl. .................... 514/206; 540/225; 540/226; 540/227
[58] Field of Search ................. 540/227, 226, 225; 514/206

[56] References Cited

U.S. PATENT DOCUMENTS 4,495,182 1/1985 Terajii et al. ................. 540/225

OTHER PUBLICATIONS

Chemical Abstracts, vol. 108: 204411t (1988).

*Primary Examiner*—Nicholas S. Rizzo
*Attorney, Agent, or Firm*—Oblon, Spivak, McClelland, Maier & Neustadt

[57] ABSTRACT

A compound having the formula:

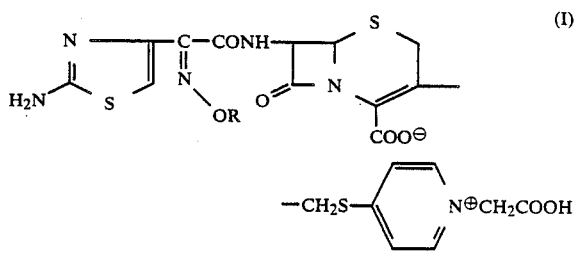

wherein R is a vinyl, phenyl or aralkyl group which may be substituted; or a pharmaceutically acceptable salt, physiologically hydrolyzable ester or solvate thereof.

6 Claims, No Drawings

CEPHALOSPORIN DERIVATIVES, AND ANTIBACTERIAL AGENTS

This is a division of application Ser. No. 028,576, filed on Mar. 30, 1987.

The present invention relates to novel cephalosporin derivatives, processes for their preparation and antibacterial agents containing them as active ingredients.

A number of cephalosporin compounds have been synthesized which have a 2-(2-aminothiazol-4-yl)-2-substituted oxyiminoacetamido group as a side chain at the 7-position of the cephem nucleus. As publications which disclose such compounds, Japanese Unexamined Patent Publication Nos. 102293/1977, 116492/1977, 137988/1978, 9296/1979, 154786/1979, 157596/1979, 154980/1980, 86187/1981, 59895/1982, 99592/1982, 192394/1982 and 74387/1983, may be mentioned. It is suggested that such compounds exhibit activities against Gram-positive bacteria and cephalosporin resistant Gram-negative bacteria including *Pseudomonas aeruginosa*, and they have excellent antibacterial activities and a broad antibacterial spectrum.

However, they do not have sufficient antibacterial activities against glucose non-fermentative Gram-negative rods such as *Pseudomonas aeruginosa, Pseudomonas cepacia, Pseudomonas maltophilia* and *Acinetobacter calcoaceticus.*

Further, Japanese Unexamined Patent Publication Nos. 89289/1980, 90590/1983, 105683/1985, 215690/1985, 17589/1986 and 134390/1986 disclose compounds having a 1-substituted pyridinio-4-ylthiomethyl group at the 3-position of the cephem nucleus and a 2-(2-aminothiazol-4-yl)-2-substituted oxyiminoacetamido group at the 7-position simultaneously. However, Japanese Unexamined Patent Publication Nos. 89289/1980, 105683/1985 and 134390/1986 neither disclose nor suggest that the cephem nucleus has a 1-carboxymethylpyridinio-4-ylthiomethyl group at its 3-position, which is the primary feature of the present invention. A compound disclosed in Japanese Unexamined Patent Publication No. 90590/1983 has a 1-lower alkoxycarbonylmethylpyridinio-4-ylthiomethyl group as a substituent at the 3-position of the cephem nucleus, and there is no suggestion that the pyridine nucleus has a carboxymethyl group at its 1-position. Further, the 1-position of the cephem nucleus is limited to a sulfoxide group. Japanese Unexamined Patent Publication No. 17589/1986 discloses that the pyridine nucleus in the substituent at the 3-position of the cephem nucleus has a carboxymethyl group at its 1-position. However, a compound disclosed in this reference has the formula:

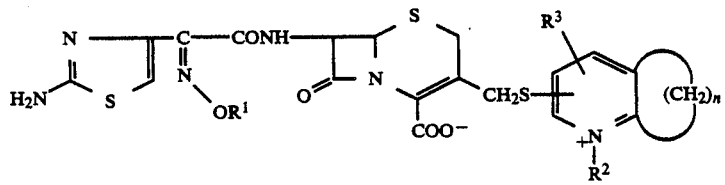

wherein $R^1$ is a straight or branched chain alkyl group having from 1 to 5 carbon atoms, a cycloalkanomethyl group having from 3 to 6 carbon atoms or

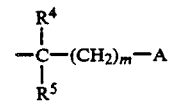

(wherein m is an integer 0 or from 1 to 3, A is a —$COR^6$ group where $R^6$ is a hydroxyl group, ..., $R^4$ and $R^5$ are a hydrogen atom or an alkyl group having from 1 to 5 carbon atoms, or $R^4$ and $R^5$ may together form a cycloalkylidene group having from 3 to 5 carbon atoms), is an alkyl group having from 1 to 5 carbon atoms, which may have a substituent including a carboxyl group, and $R^3$ is a hydrogen atom, an alkyl or alkenyl group having from 1 to 5 carbon atoms or an oxygen atom. Thus, the 1-carboxymethylpyridinio group is further substituted or forms a fused ring. Further, this reference neither discloses nor suggests, as a substituent in the substituted oxyimino group, a vinyl, phenyl or aralkyl group which may be substituted, which is the second feature of the present invention. Only Japanese Unexamined Patent Publication No. 215690/1985 discloses a 1-carboxymethylpyridinio-4-ylthiomethyl group as a substituent at the 3-position of the cephem nucleus, and only a methyl, ethyl, allyl, carboxymethyl or 1-carboxy-1-methylethyl group is disclosed as the substituent of the substituted oxyimino group. This reference does not disclose at all, as the substituent in the substituted oxyimino group, a vinyl, phenyl or aralkyl group which may be substituted.

These publications disclose compounds having a 1-substituted pyridinio-4-ylthiomethyl group, but do neither disclose compounds having, as the substituent in the substituted oxyimino group, a vinyl, phenyl or aralkyl group which may be substituted, nor mention any syntheses thereof.

β-Lactam antibiotics exhibit selective toxicity against bacteria only and present no substantial effects against animal cells, and they have been widely used for the treatment of infectious diseases caused by bacteria as antibiotics having no substantial side effects. Thus, they are highly useful drugs.

However, in recent years, glucose non-fermentative Gram-negative rods, particularly *Pseudomonas aeruginosa*, have been frequently isolated from immuno-compromised patients, as causative organisms of refractory infections and have posed various problems. Therefore, it has been desired to develop an antimicrobial agent having an improved activity against such bacteria.

It is an object of the present invention to provide novel cephalosporin derivatives having excellent antibacterial activities.

As a result of an extensive research, it has been found that novel cephalosporin derivatives having a 1-carboxymethylpyridinio-4-ylthiomethyl group at the 3-position of the cephem nucleus and a 2-(2-aminothiazol-4-yl)-2-substituted oxyiminoacetamido group at the 7-position of the cephem nucleus, have excellent antibacterial activities against Gram-positive bacteria and Gram-negative bacteria. They have strong activities

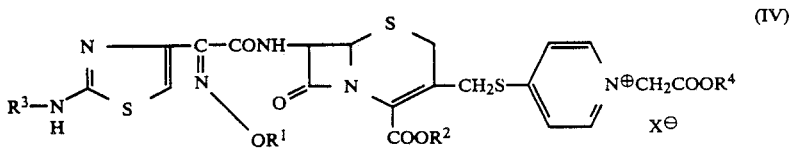

and a broad antibacterial spectrum against glucose non-fermentative Gram-negative rods, such as methicilline resistant *Staphylococcus aureus* JS1, *Pseudomonas aeruginosa*, *Pseudomonas cepacia*, and *Acinetobacter calcoaceticus* as compared with ceftazidime and cefotaxime, and they have excellent stability against β-lactamase. The present invention has been accomplished on the basis of these discoveries.

The present invention provides a compound having the formula:

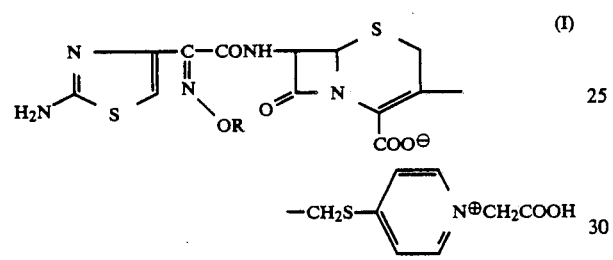

wherein R is a vinyl, phenyl or aralkyl group which may be substituted; or a pharmaceutically acceptable salt, physiologically hydrolyzable ester or solvate thereof Further, the present invention provides a process for preparing the compound of the formula I, or a phamaceutically acceptable salt, physiologically hydrolyzable ester or solvate thereof, comprises reacting a compound having the formula:

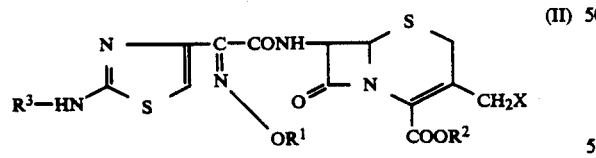

wherein $R^1$ is a vinyl, phenyl or aralkyl group which may be substituted, $R^2$ is a hydrogen atom or a carboxyl-protecting group, $R^3$ is a hydrogen atom or an amino-protecting group, X is a leaving group, (provided that the substituent of $R^1$ is optionally protected), or a salt thereof, with a compound having the formula:

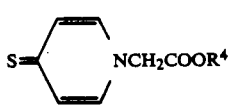

wherein $R^4$ is a hydrogen atom or a carboxyl-protecting group, to form a compound having the formula:

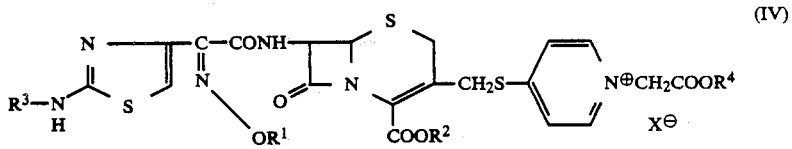

wherein $R^1$, $R^2$, $R^3$ and $R^4$ are as defined above, and $X^\ominus$ is an anion, and optionally removing the protecting groups.

Another process of the preparation of the compound of the formula I, or a pharmaceutically acceptable salt, physiologically hydrolyzable ester or solvate thereof, comprises acylating a compound having the formula:

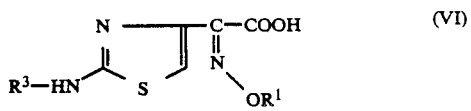

wherein each of $R^2$ and $R^4$ is a hydrogen atom or a carboxyl-protecting group, $X^\ominus$ is an anion, or a salt thereof, with a carboxylic acid having the formula:

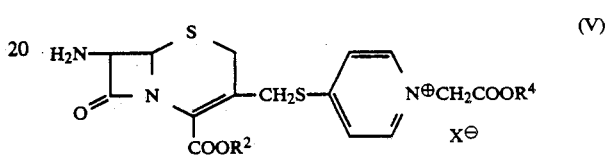

wherein $R^1$ is a vinyl, phenyl or aralkyl group which may be substituted, and $R^3$ is a hydrogen atom or an amino-protecting group, (provided that the substituent of $R^1$ is optionally protected), or a reactive derivative thereof to form a compound having the formula:

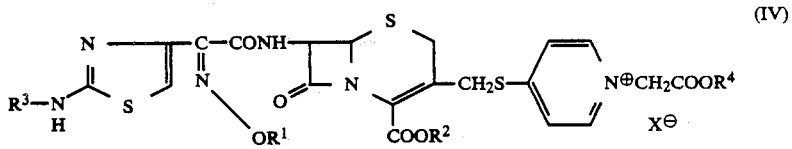

wherein $R^1$, $R^2$, $R^3$, $R^4$ and $X^\ominus$ are as defined above, and optionally removing the protecting groups.

The present invention also provides an antibacterial agent comprising an antibacterially effective amount of the compound of the formula I and a pharmaceutically acceptable carrier.

Now, the symbols and terms used in the present specification will be explained.

The substituent R in the compound of the formula I represents a vinyl, phenyl or aralkyl group, which may be substituted.

R may have one or more substituents which may be the same or different, selected from the group consisting of an alkyl group having from 1 to 4 carbon atoms, a hydroxyl group, an alkoxy group having from 1 to 4 carbon atoms, an acetoxy group, a carboxyl group, a substituted phenyl group and a halogen atom such as fluorine, chlorine and iodine.

As the vinyl group which may be substituted, there may be mentioned a vinyl, 1-propenyl, isopropenyl, 2-methyl-1-propenyl, 1-carboxyvinyl, 2-carboxyvinyl, 1-carboxy-1-propenyl or 1-carboxy-2-methyl-1-propenyl group, or a styryl or α-carboxystyryl group which may have one or more substituents in the benzene ring.

As the phenyl group which may be substituted, there may be mentioned a phenyl, 2-hydroxyphenyl, 3-hydroxyphenyl, 4-hydroxyphenyl, 2-acetoxyphenyl, 3-acetoxyphenyl, 4-acetoxyphenyl, 2-chlorophenyl, 3-chlorophenyl, 3-carboxyphenyl, 4-carboxyphenyl, 3,4-dihydroxyphenyl or 3,4-diacetoxyphenyl group.

As the aralkyl group which may be substituted, there may be mentioned a benzyl, 4-hydroxybenzyl, 3-hydroxybenzyl, 4-acetoxybenzyl, 3-acetoxybenzyl, 3,4-dihydroxybenzyl, 3,4-diacetoxybenzyl, 3,4,5-trihydroxybenzyl, 3,4,5-triacetoxybenzyl, α-carboxybenzyl, α-carboxy-4-hydroxybenzyl, α-carboxy-3-hydroxybenzyl, α-carboxy-4-acetoxybenzyl, α-carboxy-3-acetoxybenzyl, α-carboxy-3,4-dihydroxybenzyl, α-carboxy-3,4-diacetoxybenzyl or α-carboxy-3,4,5-triacetoxybenzyl group.

Further, the moiety

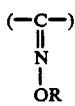

in the oxyimino group in the formula I, includes a syn-isomer (Z configuration:

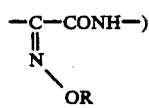

and an anti-isomer (E configuration:

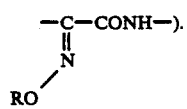

Generally, the syn-isomer (Z configuration) exhibits superior antibacterial activities. In this specification, the OR group represents the syn-isomer (Z configuration) in all cases. The nomenclature for E and Z configurations is given in Journal of the American Chemical Society, Vol. 90, p 509 (1968).

The compounds of the formula I may be converted to non-toxic salts or physiologically hydrolyzable non-toxic esters thereof by usual methods. The non-toxic salts of the compounds of the formula I mean pharmaceutically acceptable usual salts, at the carboxyl groups at the 4- and 7-positions of the cephem nucleus or at the amino group in the thiazole ring at the 7-position of the cephem nucleus. For instance, a salt of a metal such as sodium, potassium, calcium, magnesium or aluminum, a salt of an organic amine such as N,N'-dibenzylethylenediamine or procaine, a salt of an inorganic acid such as hydrochloric acid, hydrobromic acid, nitric acid, sulfuric acid or perchloric acid, a salt of an organic acid such as acetic acid, lactic acid, propionic acid, maleic acid, fumaric acid, malic acid, tartaric acid or citric acid, a salt of a sulfonic acid such as methanesulfonic acid, isethionic acid or p-toluenesulfonic acid and a salt of an amino acid such as glutamic acid, aspartic acid, lysine or arginine, may be mentioned.

The non-toxic esters of the compounds of the formula I mean pharmaceutically acceptable usual esters at the carboxyl groups at the 4-position of the cephem nucleus. For instance, an alkanoyloxymethyl group such as an acetoxymethyl group or a pivaloyloxymethyl group, an alkoxycarbonyloxyalkyl group such as a 1-(ethoxycarbonyloxy)ethyl group, a phthalidyl group, and a 5-substituted-2-oxo-1,3-dioxol-4-ylmethyl group such as a 5-methyl-2-oxo-1,3-dioxol-4-ylmethyl group, may be mentioned.

Now, the processes for the preparation of the compounds of the present invention will be described.

The compound of the formula I may be prepared by either one of the following processes A and B.

Process A

The compound of the formula I of the present invention can be prepared by reacting a compound having the formula:

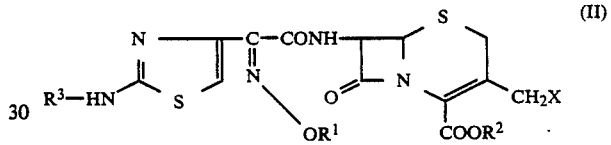

wherein $R^1$ is a vinyl, phenyl or aralkyl group which may be substituted, $R^2$ is a hydrogen atom or a carboxyl-protecting group, $R^3$ is a hydrogen atom or an amino-protecting group, X is a leaving group, (provided that the substituent of $R^1$ is optionally protected), or a salt thereof, with a compound having the formula:

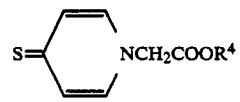

wherein $R^4$ is a hydrogen atom or a carboxyl-protecting group, to form a compound having the formula:

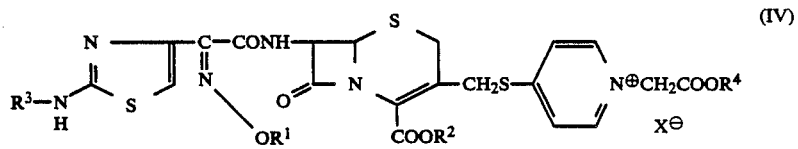

wherein $R^1$, $R^3$ and $R^4$ are as defined above, and $X^{\ominus}$ is an anion, and optionally removing the protecting groups.

The substituent X in the formula II represents a leaving group. Specifically, there may be mentioned a halogen atom such as chlorine, bromine or iodine, an acetoxy group, a carbamoyloxy group, a trifluoromethanesulfonyloxy group and a p-toluenesulfonyloxy group. Particularly preferred is a bromine atom, an iodine atom or an acetoxy group.

Process B

The compound of the formula I of the present invention can also be prepared by acylating a compound having the formula:

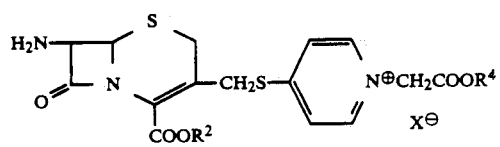

(V)

wherein each of R² and R⁴ is a hydrogen atom or a carboxyl-protecting group, X⊖ is an anion, or a salt thereof, with a carboxylic acid having the formula:

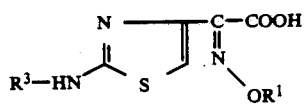

(VI)

wherein R¹ is a vinyl, phenyl or aralkyl group which may have substituent, and R³ is a hydrogen atom or an amino-protecting group, (provided that the substituent of R¹ is optionally protected), or a reactive derivative thereof to form a compound having the formula:

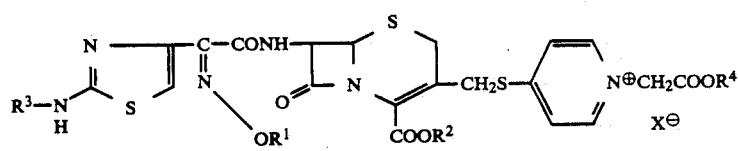

(IV)

wherein R¹, R², R³, R⁴ and X⊖ are as defined above, and optionally removing the protecting groups.

Further, a compound of the present invention having an acetoxy group as the substituent of R may be prepared by the acylation with a carboxylic acid of the formula VI or a reactive derivative thereof wherein the substituent of R¹ is an acetoxy group to obtain a compound of the formula II or IV, reacting the compound of the formula II with the 1-carboxymethyl-4-pyridothione derivative of the formula III to lead it to a compound of the formula IV, and optionally removing the protective groups. Furthermore, it may also be produced by acetylating a compound of the formula I having a hydroxyl group as the substituent of R or acetylating a compound of the formula II or IV having a hydroxyl group to give a compound of the formula II or IV having an acetoxy group, reacting the compound of the formula II with a 1-carboxymethyl-4-pyridone derivative of the formula III leading to a compound of the formula IV, and optionally removing the protective groups by a conventional method.

Now, processes A and B for the preparation of the compounds of the formula I of the present invention, will be described in detail.

Process A

The reaction of the compound of the formula II with the 4-pyridothione derivative of the formula III, may be conducted in an organic solvent such as methylene chloride, chloroform, ethyl ether, ethyl acetate, butyl acetate, tetrahydrofuran, acetonitrile, N,N-dimethylformamide or dimethylsulfoxide, or in a mixture of such solvents. When R⁴ in the formula III is a hydrogen atom, the 4-pyridothione derivative may be employed as a metal carboxylate such as sodium, potassium, calcium, magnesium and silver carboxylate, or an organic ammonium such as triethyl ammonium and diisopropyl ammonium carboxylate. Further, the 4-pyridothione derivative of the formula III may be employed in a form silylated with a silylating agent such as N,O-bis(trimethylsilyl)acetamide. The reaction is conducted by using from 1 to 2 mols of the 4-pyridothione derivative of the formula III relative to 1 mol of the compound of the formula II. The reaction temperature and the reaction time are from 0° to 40° C. and from 0.5 to 5 hours, respectively.

The reaction of a compound of the formula II wherein X is an acetoxy group, with the 4-pyridothione derivative of the formula III, may be conducted in a solvent such as water, phosphate buffer solution, acetone, acetonitrile, methanol, ethanol, tetrahydrofuran, dioxane, N,N-dimethylformamide or dimethylsulfoxide, or in a mixture of such solvents. The reaction is preferably conducted under a neutral condition at a reaction temperature of from room temperature to 90° C. for the reaction time of from 1 to 10 hours. The reaction is facilitated by conducting it in the presence of from 1 to 20 mols of an iodide such as sodium iodide, a thiocyanate such as sodium thiocyanate, or a quarternary ammonium salt such as trimethylbenzyl ammonium bromide, relative to 1 mol of the compound of the formula II. The reaction may be conducted in the presence of 1 to 50 mols of an acid such as sulfuric acid, p-toluenesulfonic acid, methanesulfonic acid, trifluoromethanesulfonic acid, chlorosulfonic acid, boron trifluoride and boron trifluoride etherate in a solvent described above at a reaction temperature of from room temperature to 60° C. for the reaction time of from 1 to 10 hours.

The compound of the formula I of the present invention may be prepared, if necessary, by removing the protecting groups from the compound of the formula IV. As the protecting groups for the carboxyl, amino and hydroxyl groups in the above formulas, protecting groups which are commonly employed in the field of β-lactam synthesis, may suitably be selected for use. The introduction and removal of the protecting groups may be conducted by employing a suitable method depending upon the type of the protecting group selected, for instance, from those described in "Protective Groups in Organic Synthesis" written by T. W. Greene published in 1981 by Wiley Company and in Protective Groups in Organic Chemistry written by J. F. W. McOmie published in 1973 by Plenum Press. As the carboxyl-protecting group, there may be mentioned t-butyl, 2,2,2-trichloroethyl, acetoxymethyl, propionyloxymethyl, pivaloyloxymethyl, 1-acetoxyethyl, 1-propionyloxyethyl, 1-(ethoxycarbonyloxy)ethyl, phthalidyl, benzyl, 4-methoxybenzyl, 3,4-dimethoxybenzyl, 4-nitrobenzyl, benzhydryl, bis(4-methoxyphenyl)methyl, 5-methyl-2-oxo-1,3-dioxol-4-ylmethyl, trimethylsilyl and t-butyldimethylsilyl. Particularly preferred are benzhydryl, t-butyl and silyl.

As the amino-protecting group, there may be mentioned, for example, trityl, formyl, chloroacetyl, trifluoroacetyl, t-butoxycarbonyl, trimethysilyl and t-butyldimethylsilyl.

As the hydroxyl-protecting group, there may be mentioned, for example, 2-methoxyethoxymethyl, methoxymethyl, methylthiomethyl, tetrahydropyranyl, phenacyl, isopropyl, t-butyl, benzyl, 4-nitrobenzyl, acetyl, 2,2,2-trichloroethoxycarbonyl, benzyloxycarbonyl, acetonide, trimethylsilyl and t-butyldimethylsilyl.

The method for the removal of the protecting groups will be described in detail. For instance, the removal of a protecting group such as trityl, formyl, t-butoxycarbonyl, benzhydryl, t-butyl or 2-methoxyethoxymethyl, may be conducted by means of an inorganic or organic acid such as hydrochloric acid, formic acid, trifluoroacetic acid, benzenesulfonic acid or p-toluenesulfonic acid. Trifluoroacetic acid is particularly preferred.

When trifluoroacetic acid is used as the acid, the reaction can be facilitated by an addition of anisole, and side reactions can be thereby suppressed.

The reaction may be conducted in a solvent which is inert to the reaction, such as water, methylene chloride, chloroform, ethylene chloride or benzene, or in a mixture of such solvents. The reaction temperature and time are suitably selected depending upon the chemical properties of the compound of the formula IV and the compound of the formula I of the present invention and the type of the protecting group to be removed. The reaction is preferably conducted under a condition ranging from an ice-cooling condition to a slightly heated condition.

The starting compound of the formula II for process A may be prepared in the following manner. The compound of the formula II can be prepared by reacting benzhydryl 7-amino-3-chloromethyl-3-cephem-4-carboxylate (synthesized in accordance with e.g. Japanese Unexamined Patent Publications No. 76089/1975, No. 86187/1981 and the Journal of Antibiotics Vol. 38, p 1738 (1985)), 7-aminocephalosporanic acid or its ester, with a carboxylic acid of the formula VI or its reactive derivative (such as its acid halide, mixed acid anhydride, activated ester, etc.).

A compound of the formula II wherein X is an iodine atom, can be prepared by reacting a compound of the formula II wherein X is a chlorine atom, with an iodide such as sodium iodide in a solvent such as acetone or N,N-dimethylformamide, under cooling with ice or at room temperature, or by reacting a compound of the formula II wherein X is an acetoxy group, with iodotrimethylsilane in a solvent such as methylene chloride, chloroform, diethyl ether, ethyl acetate, butyl acetate, tetrahydrofuran, acetonitrile, N,N-dimethylformamide, or dimethylsulfoxide, or in a mixture of such solvent in accordance with the method described in Tetrahedron Letters Vol. 22, p 3915 (1981). The product may be used for the subsequent reaction without or after isolation.

The 1-benzhydroxycarbonylmethyl-4-pyridothione of the formula III can be prepared by the method described in J. Chem. Soc., p 3610 (1958).

For instance, 4-hydroxypyridine is reacted with benzhydryl α-chloroacetate in a solvent such as N,N-dimethylformamide in the presence of potassium carbonate at a temperature of from 40° to 80° C. to form 1-benzhydryloxycarbonylmethyl-4-pyridone, followed by a reaction with phosphorus pentasulfide in a solvent such as tetrahydrofuran at a temperature of from 40° to 80° C. to obtain the product of the formula III.

The 2-(2-aminothiazol-4-yl)-2-substituted oxyiminoacetic acid derivative of the formula VI, can be prepared by using a 2-(2-aminothiazol-4-yl)glyoxylic acid derivative or 2-(2-aminothiazol-4-yl)-2-hydroxyimino acetate derivative by a method disclosed in e.g. Journal of the Japanese Chemical Society p 785–801 (1981).

Process B

The compound of the formula IV may be prepared by reacting the compound of the formula V with the carboxylic acid of the formula VI or its reactive derivative (such as its acid halide, mixed anhydride or activated ester) in a solvent inert to the reaction such as water, acetone, dioxane, acetonitrile, tetrahydrofuran, methylene chloride, chloroform, ethylene chloride, benzene, ethyl acetate, N,N-dimethylformamide or dimethylsulfoxide, or in a mixture of such solvents.

The reaction is conducted by using from 1 to 1.5 mols of the carboxylic acid of the formula VI or its reactive derivative relative to 1 mol of the compound of the formula V, and the reaction temperature is from −40° to 40° C.

When an acid halide is used as the reactive derivative of the formula VI, the reaction is preferably conducted in the presence of an acid-absorbing agent such as triethylamine, N-methylmorphorine, N,N-dimethylaniline or pyridine.

The acid halide-forming reaction is carried out by using from 1 to 10 mols, preferably from 1 to 1.5 mols of the halogenating agent such as thionyl chloride, phosphorus trichloride, phosphorus tribromide, phosphorus pentachloride, phosphorus oxychloride, oxalylchloride or phosgene, at a reaction temperature of from −40° to 100° C., preferably from −20° to 20° C. for a reaction time of from 10 to 120 minutes.

The mixed acid anhydride-forming reaction is conducted by using from 1 to 1.2 mols of a chloroformate such as methyl chloroformate, ethyl chloroformate or isobutyl chloroformate in the presence of from 1 to 1.2 mols of an acid-absorbing agent such as triethylamine, N-methylmorphorine, N,N-dimethylaniline or pyridine, relative to 1 mol of the carboxylic acid of the formula VI. The reaction temperature is from −40° to 20° C., preferably from −20° to 5° C. The reaction time is from 10 to 60 minutes.

The active ester-forming reaction is conducted by using from 1 to 1.2 mols of a N-hydroxy compound (such as N-hydroxysuccinimide or 1-hydroxybenzotriazole) or a phenol compound (such as 4-nitrophenol, 2,4-dinitrophenol or 2,4,5-trichlorophenol) and from 1 to 1.4 mols of N,N'-dicyclohexylcarbodiimide, relative to 1 mol of the carboxylic acid of the formula VI. The reaction temperature is from −10° to 50° C. The reaction time is from 0.5 to 2 hours.

When the carboxylic acid of the formula VI is used in the form of a free acid in the acylation reaction, the compound of the formula IV may be prepared in the presence of a condensation agent such as a carbodiimide such as N,N'-dicyclohexylcarbodiimide, or phosphorus oxychloride, an phosphorus oxychloride adduct of N,N-dimethylformamide. The preparation of the compound of the formula I of the present invention from the compound of the formula IV, is substantially the same as in process A.

The starting compound of the formula V in process B, may be prepared by a method disclosed in e.g. Cephalosporins and Penicillins, Academic Press, p 151–171, (1972) written by Flynn. For instance, a 7-acylamino-3-halomethyl-3-cephem-4-carboxylate derivative (prepared in accordance with Japanese Unexamined Patent Publication No. 72590/1983 or No. 154588/1983), a 7-acylamino cephalosporanic acid derivative or a 7-aminocephalosporanic acid, is reacted with the 1-carboxymethyl-4-pyridothione derivative of the formula III to obtain a compound having the formula:

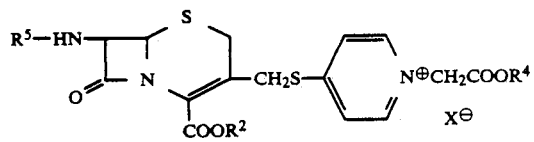

wherein each of $R^2$ and $R^4$ is a hydrogen atom or a carboxyl-protecting group, $R^5$ is a hydrogen atom or a acyl group, $X^\ominus$ is an anion, optionally followed by deacylation.

The deacylation reaction is commonly known in this field. When $R^5$ in the compound of the above formula is, for example, a phenylacetyl, phenoxyacetyl or aminoadipyl group, the deacylation is conducted in accordance with a method disclosed in Japanese Examined Patent Publication No. 20319/1974. For instance, the $R^5$ group can be removed by reacting the compound with phosphorus pentachloride or phosphorus oxychloride in a solvent such as benzene, toluene, ethyl acetate, methylene chloride or ethylene chloride, or in a mixture of such solvents in the presence of an acid-absorbing agent such as pyridine, triethylamine, sodium hydrogencarbonate or potassium hydrogencarbonate at a temperature of from −80° to 50° C., preferably from −65° to 0° C. for from 0.5 to 2 hours, followed by treatment with a lower alcohol such as methanol, ethanol or propanol, and then a hydrolysis.

The removal of the phenylacetyl, phenoxyacetyl or aminoadipyl group can be conducted by reacting penicillin G acylase or fixed penicillin G acylase in water or in a mixture of water and an organic solvent such as acetone, acetonitrile, methanol, ethanol or tetrahydrofuran at a pH of from 7 to 8, preferably from 7.5 to 7.8 in accordance with the method described in Japanese Patent Application No. 291431/1986 by the present inventors. This reaction is preferably conducted at a constant pH level by adding a base such as lithium hydroxide, sodium hydroxide, potassium hydroxide, triethylamine, tripropylamine or pyridine.

The in vitro antibacterial activities of the compounds of the present invention against various microorganisms, were measured by the following agar plate dilution method. One platinum loopfull of each test microorganism incubated overnight in Mueller Hinton broth, was inoculated to Mueller Hinton agar (inoculum size: $10^6$ CFU/ml) Such culture media containing various antibiotics in various concentrations were prepared After incubation at 37° C. for 16 hours, the minimum inhibitory concentrations (MIC: μg/ml) were measured. As comparative compounds, cefotaxime, oeftazidime and the compounds disclosed in Example 2 of Japanese Unexamined Patent Publication No. 215690/1985 e.g. sodium 7-[2-(2-aminothiazol-4-yl)-2-ethoxyiminoacetamido]-3-(1-carboxylatemethylpyridinio-4-yl)thiomethyl-3-cephem-4-carboxylate (hereinafter referred to simply as "Reference Example A") were employed. The results are shown in the following table.

TABLE

| Test microorganism | Minimum Inhibitory Concentration (MIC: μg/ml) | | | | | | |
|---|---|---|---|---|---|---|---|
| | Compound of Ex. 1 | Compound of Ex. 2 | Compound of Ex. 3 | Compound of Ex. 4 | Compound of Ex. 5 | Compound of Ex. 6 | Compound of Ex. 7 |
| 1. S. aureus 209P NIHJ-JC1 | 3.12 | 0.39 | 12.5 | 0.39 | 0.78 | 1.56 | 0.39 |
| *2. S. aureus JS1 | 50 | 50 | 50 | 6.25 | 6.25 | 25 | 12.5 |
| 3. S. aureus BB5703 | 25 | 1.56 | 25 | 3.12 | 3.12 | 6.25 | 3.12 |
| 4. S. epidermidis IAM12012 | 1.56 | 0.20 | 6.25 | 0.78 | 1.56 | 3.12 | 0.2 |
| 5. M. luteus ATCC9341 | 1.56 | 0.025 | 3.12 | 0.39 | 0.78 | 3.12 | 0.1 |
| 6. C. freundii GN346/16 | 0.10 | 0.78 | 1.56 | 0.20 | 0.39 | 0.39 | 1.56 |
| 7. E. coli NIHJ JC2 | 0.10 | 1.56 | 1.56 | 0.05 | 0.10 | 0.2 | 0.78 |
| *8. E. coli CSH2 (RK1) | 0.05 | 0.20 | 0.78 | 0.05 | 0.05 | 0.05 | 0.78 |
| 9. K. pneumoniae PCI-602 | <0.006 | 0.0125 | <0.006 | <0.006 | <0.006 | <0.006 | 0.025 |
| *10. E. coli CSH(RE45) | 0.10 | 0.20 | 0.78 | 0.025 | 0.05 | 0.05 | 0.78 |
| *11. K. oxytoca GN10650 | 0.20 | 12.5 | 0.78 | 0.78 | 0.05 | 0.2 | 25 |
| *12. K. pneumoniae No. 42 | 0.20 | 1.56 | 1.56 | 0.20 | 0.20 | 0.1 | 3.12 |
| 13. P. vulgaris HX-19 | <0.006 | <0.006 | 0.0125 | 0.025 | 0.025 | 0.1 | <0.006 |
| *14. P. vulgaris No. 33 | 0.0125 | 1.56 | 0.10 | 0.20 | 0.05 | 0.1 | 0.78 |
| 15. S. marcescens IAM 1184 | <0.006 | 1.56 | 0.39 | 0.10 | 0.10 | 0.2 | 0.78 |
| *16. C. freundii GN346 | 25 | 25 | 100 | 6.25 | 25 | 25 | 50 |
| 17. E. cloacae 963 | 0.10 | 1.56 | 1.56 | 0.10 | 0.10 | 0.39 | 3.12 |
| *18. E. cloacae Nek 39 | 0.78 | 6.25 | 6.25 | 0.78 | 0.20 | 0.78 | 12.5 |
| *19. E. coli GN5482 | 0.20 | 0.78 | 0.78 | 0.39 | 0.20 | 0.39 | 1.56 |
| *20. M. morganii GN5407 | 0.0125 | 1.56 | 0.78 | 0.10 | 0.10 | 0.2 | 0.78 |
| *21. S. marcescens No. 16-2 | 1.56 | 12.5 | 6.25 | 6.25 | 0.78 | 1.56 | 12.5 |
| 22. Ps. aeruginosa IFO3445 | 1.56 | 25 | 3.12 | 3.12 | 0.39 | 0.78 | 12.5 |
| 23. Ps. aeruginosa AK 109 | 3.12 | 25 | 6.25 | 1.56 | 0.78 | 0.78 | 25 |
| 24. Ps. aeruginosa AKR17 | >100 | >100 | >100 | >100 | 1.56 | 1.56 | >100 |
| 25. Ps. cepacia 23 | 1.56 | 12.5 | 3.12 | 0.39 | <0.006 | 0.025 | 3.12 |
| *26. Ps. maltophilia GN 12873 | >100 | >100 | >100 | >100 | >100 | >100 | >100 |
| 27. A. calcoaceticus No. 4 | 50 | 25 | 50 | 1.56 | 0.20 | 0.39 | 3.12 |

| Test microorganism | Minimum Inhibitory Concentration (MIC: μg/ml) | | |
|---|---|---|---|
| | Reference Example A | Ceftazidime | Cefotaxime |
| 1. S. aureus 209P NIHJ-JC1 | 0.39 | 6.25 | 1.56 |
| *2. S. aureus JS1 | 100 | 25 | 25 |
| 3. S. aureus BB5703 | 3.12 | 12.5 | 3.12 |
| 4. S. epidermidis IAM12012 | 0.05 | 3.12 | 1.56 |
| 5. M. luteus ATCC9341 | 0.10 | 0.78 | 0.10 |
| 6. C. freundii GN346/16 | 0.10 | 0.20 | 0.10 |
| 7. E. coli NIHJ JC2 | 0.05 | 0.20 | 0.05 |
| *8. E. coli CSH2 (RK1) | 0.025 | 0.10 | 0.025 |
| 9. K. pneumoniae PCI-602 | <0.006 | <0.006 | <0.006 |

TABLE-continued

|  |  | | | |
|---|---|---|---|---|
| *10. | E. coli CSH(RE45) | 0.05 | 0.10 | 0.10 |
| *11. | K. oxytoca GN10650 | 3.12 | 0.20 | 0.39 |
| *12. | K. pneumoniae No. 42 | 0.050 | 0.39 | 0.05 |
| 13. | P. vulgaris HX-19 | <0.006 | 0.025 | <0.006 |
| *14. | P. vulgaris No. 33 | 0.05 | 0.05 | 0.025 |
| 15. | S. marcescens IAM 1184 | 0.05 | 0.025 | 0.10 |
| *16. | C. freundii GN346 | 25.0 | 25 | 12.5 |
| 17. | E. cloacae 963 | 0.10 | 0.20 | 0.10 |
| *18. | E. cloacae Nek 39 | 1.56 | 3.12 | 3.12 |
| *19. | E. coli GN5482 | 0.20 | 1.56 | 0.39 |
| *20. | M. morganii GN5407 | 0.05 | 0.10 | 0.10 |
| *21. | S. marcescens No. 16-2 | 6.25 | 1.56 | 12.5 |
| 22. | Ps. aeruginosa IFO3445 | 6.25 | 0.39 | 12.5 |
| 23. | Ps. aeruginosa AK 109 | 12.5 | 1.56 | 12.5 |
| 24. | Ps. aeruginosa AKR17 | >100 | >100 | >100 |
| 25. | Ps. cepacia 23 | 6.25 | 0.78 | 6.25 |
| *26. | Ps. maltophilia GN 12873 | >100 | 100 | >100 |
| 27. | A. calcoaceticus No. 4 | 100 | 6.25 | 25 |

*β-Lactamase-producing strains

Thus, the compounds of the present invention, particularly the compounds of Examples 5 and 6, have excellent antibacterial activities and a broad antibacterial spectrum against sensitive and resistant Gram-positive bacteria and Gram-negative bacteria particularly glucose non-fermentative Gram-negative rods, such as Pseudomonas aeruginosa, Pseudomonas cepacia, and Acinetobacter calcoaceticus.

Thus, the compounds of the formula I and non-toxic salts and physiologically hydrolyzable non-toxic esters thereof are useful as antibacterial agents.

The compounds of the present invention may be mixed with a carrier of solid or liquid excipient, and may be used in the form of a pharmaceutical formulation suitable for parenteral administration, oral administration or external administration. As the pharmaceutical formulations, there may be mentioned liquid formulations such as injection solutions, syrups and emulsions, solid formulations such as tablets, capsules and granules and formulations for external application such as ointments and suppositories. Further, these formulations may contain commonly employed additives such as assisting agents, stabilizers, wetting agents, emulsifying agents, absorption-promoting agents or surfactants. As such additives, distilled water for injection, a Ringer solution, glucose, sucrose syrup, gelatin, edible oil, coconut oil, ethylene glycol, sucrose, corn starch, magnesium stearate and talc, may be mentioned.

Further, the compounds of the present invention can be used as antibacterial agents for the treatment of human infectious diseases caused by Gram-negative bacteria including glucose non-fermentative Gram-negative rods such as Pseudomonas aeruginosa, Pseudomonas cepacia, and Acinetobacter calcoaceticus. The dose may vary depending upon the age, sex and condition of the patient, and is usually within a range of from 1 to 100 mg/kg per day. It is preferred to administer a daily dose of from 5 to 30 mg/kg in 2 to 4 times.

Now, the present invention will be described in further detail with reference to Examples. However, it should be understood that the present invention is by no means restricted to these specific Examples.

EXAMPLE 1

Preparation of
7-[2-(2-aminothiazol-4-yl)-2-(1-carboxy-1-vinyloxyimino)acetamido]-3-(1-carboxymethylpyridinio-4-yl)thiomethyl-4-carboxylate (syn-isomer)

(A) 5.06 g (9.76 mmol) of 2-(1-t-butoxycarbonyl-1-vinyloxyimino)-2-(2-tritylaminothiazol-4-yl)acetic acid (syn-isomer) and 4.05 g (9.76 mmol) of benzhydryl 7-amino-3-chloromethyl-3-cephem-4-carboxylate were dissolved in 100 ml of methylene chloride, and 5.56 ml (43.9 mmol) of N,N-dimethylaniline was dropwise added thereto under cooling with ice. Then, 1.07 ml (11.5 mmol) of phosphorus oxychloride was dropwise added thereto. The mixture was stirred at room temperature for 1 hour, then washed sequentially with 0.5 N hydrochloric acid and a saturated sodium chloride aqueous solution and dried over anhydrous sodium sulfate. The solvent was distilled off under reduced pressure, and ether was added to the residue to obtain 8.7 g (yield: 96.7%) of benzhydryl 3-chloromethyl-7-[2-(1-t-butoxycarbonyl-1-vinyloxyimino)-2-(2-tritylaminothiazol-4-yl)acetamido]-3-cephem-4-carboxylate (syn-isomer).

IR(KBr) cm$^{-1}$: 700, 1150, 1520, 1720, 1790, 2960, 3400:

NMR(DMSO-d$_6$)δ: 1.48(9H, s), 3.47 and 3.75(2H, ABq, J=18Hz), 4.45(2H, br s), 5.19(1H, br s), 5.27(1H, d, J=4.5Hz), 5.35(1H, br s), 5.77(1H, dd, J=4.5 and 7.5Hz), 6.92(1H, s), 6.95(1H, s), 7.30(25H, m), 8.86(1H, br s), 9.79(1H, d, J=7.5Hz).

(B) 4 g (4.34 mmol) of the compound obtained in the above reaction (A), was dissolved in 80 ml of acetone, and 3.25 g (21.7 mmol) of sodium iodide was added thereto under cooling with ice. The mixture was stirred at room temperature for 1 hour. The solvent was distilled off under reduced pressure, and 80 ml of ethyl acetate was added to the residue. The solution was washed sequentially with water, a 10% sodium thiosulfate aqueous solution and a saturated sodium chloride aqueous solution, and dried over anhydrous sodium sulfate. The solvent was distilled off under reduced pressure, and ether was added to the residue to obtain 3.98 g (yield: 90.5%) of benzhydryl 3-iodomethyl-7-[2-(1-t-butoxycarbonyl-1-vinyloxyimino)-2-(2-tritylaminothiazol-4yl)acetamido]-3-cephem-4-carboxylate (syn-isomer), which was used for the next reaction without purification.

(C) 608 mg (0.6 mmol) of the compound obtained in the above reaction (B) was dissolved in 5 ml of N,N-dimethylformamide, and 194 mg (0.6 mmol) of 1-benzhydryloxycarbonylmethyl-4-pyridothione was added. The reaction solution was stirred at room temperature for 1 hour, and 50 ml of ethyl acetate was added thereto. The reaction solution was washed sequentially with 20 ml of 0.1 N hydrochloric acid, 20 ml of a saturated sodium hydrogencarbonate aqueous solution and 20 ml of a saturated sodium chloride aqueous solution, and dried over anhydrous sodium sulfate. The solvent was distilled off, and ethyl ether was added to the residue to obtain 610 mg of benzhydryl 7-[2-(1-t-butoxycarbonyl-1-vinyloxyimino)-2-(2-tritylaminothiazol-4-yl)acetamido]-3-(1-benzhydryloxycarbonylmethylpyridinio-4-yl) thiomethyl-3-cephem-4-carboxylate iodide (syn-isomer), which was used for the next reaction without purification.

(D) 610 mg of the compound obtained in the above reaction (C) was dissolved in 7 ml of methylene chloride and 1.4 ml of anisol, and cooled to 0° C. A solution comprising 14 ml of trifluoroacetic acid and 7 ml of methylene chloride, which was preliminary cooled to 0° C., was simultaneously added thereto at once, and the mixture was stirred for 1 hour at the same temperature. The solvent was distilled off under reduced pressure, and ethyl ether was added to the residue to obtain 350 mg of a crude product. The crude product was purified by a reversed phase column chromatography (LC Sorb RP-18, manufactured by Kemco Co.; elution with a 20% methanol aqueous solution) to obtain 75 mg (yield: 20.1%) of the above identified compound.

MP: 155° C. (decomposed):
IR(KBr)cm$^{-1}$: 1370, 1630, 1770, 3400:
NMR(D$_2$O) δ: 3.35 and 3.75(2H, ABq, J=18Hz), 4.10 and 4.41(2H, ABq, J=14Hz), 4.99(2H, s), 5.20(1H, br s), 5.28(1H, br s), 5.30(1H, d, J=4Hz), 5.79(1H, d, J=4Hz), 7.11(1H, s), 7.75(2H, d, J=7Hz), 8.29(2H, d, J=7Hz).

EXAMPLE 2

Preparation of monosodium 7-[2-(2-aminithiazol-4-yl)-2-benzyloxyiminoacetamide]-3-(1-caboxylatemethylpyridinio-4-yl)thiomethyl-3-cephem-4-carboxylate (syn-isomer)

(A) 171 mg (0.17 mmol) of benzhydryl 3-iodomethyl-7-[2-benzyloxyimino-2-(2-tritylaminothizol-4-yl)-acetamido] -3-cephem-4-carboxylate (syn-isomer) was dissolved in 1 ml of N,N-dimethylformamide, and 58 mg (0.179 mmol) of 1-benzhydryloxycarbonylmethyl-4-pyridothione was added thereto. The mixture was stirred at room temperature for 1 hour. 10 ml of ethyl acetate was added to the reaction solution, and the mixture was washed with 0.1 N hydrochloric acid and a saturated sodium chloride aqueous solution. After the organic layer was dryed over anhydrous sodium sulfate, the solvent was distilled off under reduced pressure. Ethyl ether was added to the residue to obtain 200 mg of 7-[2-benzyloxyimino-2-(2-tritylaminothiazol-4-yl)acetamido]-3-(1-benzhydryloxycarbonylmethylpyridinio-4-yl)thiomethyl-3-cephem-4-carboxylate iodide (syn-isomer), which was used for the next reaction without purification.

(B) 200 mg of the compound obtained in the above reaction (A), was dissolved in 4 ml of methylene chloride and 0.8 ml of anisol, and cooled to 0° C. A solution comprising 8 ml of trifluoroacetic acid and 4 ml of methylene chloride which was preliminary cooled to 0° C., was added thereto at once, and the mixture was stirred for 1 hour at the same temperature. The solvent was distilled off under reduced pressure, and ether was added to the residue to obtain 120 mg of a crude product. The crude product was suspended in a small amount of water and adjusted to pH 7.1 with sodium hydrogencarbonate, and purified by a reversed phase column chromatography (LC Sorb RP-18, manufactured by Kemco Co.; elution with a 5% methanol aqueous solution) to obtain 26.2 mg (yield: 23.3%) of the above identified compound.

MP: 170° C. (decomposed):
IR(KBr)cm$^{-1}$: 1380, 1630, 1760, 3400:
NMR(D$_2$O) δ: 3.18 and 3.56(2H, ABq, J=18Hz), 4.20(2H, br s), 4.90(2H, s), 5.08(1H, d, J=4.5Hz), 5.20(2H, s), 5.69(1H, d, J=4.5Hz), 6.88(1H, s), 7.35(5H, s), 7.70(2H, d, J=7Hz), 8.26(2H, d, J=7Hz).

EXAMPLE 3

Preparation of disodium 7-[2-(2-aminothiazol-4-yl)-2-(α-carboxylatebenzyloxyimino)acetamide]-3-(1-caboxylatemethylpyridinio-4-yl)thiomethyl-3-cephem-4-carboxylate (syn-isomer)

(A) 730 mg (1 mmol) of 2-(α-benzhydryloxycarbonylbenzyloxyimino)-2-(2-tritylaminothiazol-4-yl)acetic acid (syn-isomer) was dissolved in 10 ml of methylene chloride, and 415 mg of benzhydryl 7-amino-3-chloromethyl-3-cephem-4-carboxylate was added thereto and cooled to 0° C. Then, 0.57 ml (4.5 mmol) of N,N-dimethylaniline was added, and 0.11 ml (1.2 mmol) of phosphorus oxychloride was dropwise added thereto. The mixture was stirred for 1 hour, and the reaction solution was washed sequentially 1 N hydrochloric acid, a saturated sodium hydrogencarbonate aqueous solution and a saturated sodium chloride aqueous solution. The organic layer was dried over anhydrous sodium sulfate, and the solvent was distilled off under reduced pressure. Ethyl ether was added to the residue to obtain 1.12 g of 3-chloromethyl-7-[2-(α-benzhydryloxycarbonylbenzyloxyimino)-2-(2-tritylaminothiazol-4-yl)acetamido]-3-cephem-4-carboxylate (syn-isomer), which was used for the next reaction without purification.

(B) 152 mg (0.135 mmol) of the compound obtained in the above reaction (A), was dissolved in 1 ml of N,N-dimethylformamide, and 48 mg (0.148 mmol) of 1-benzhydryloxycarbonylmethyl-4-pyridothione was added thereto. The mixture was stirred at room temperature for 1 hour. 10 ml of ethyl acetate was added thereto, and washed with 0.1 N hydrochloric acid and a saturated sodium chloride aqueous solution. The extract was dried over anhydrous sodium sulfate, and the solvent was distilled off under reduced pressure. Then, ethyl ether was added to the residue to obtain 165 mg of 7-[2-(α-benzhydryloxycarbonylbenzyloxyimino)-2-(2-tritylaminothiazol-4-yl)acetamide]-3-(1-benzhydryloxycarbonylmethylpyridinio-4-yl)thiomethyl-3-cephem-4-carboxylate chloride (syn-isomer), which was used for the next reaction without purification.

(C) 165 mg of the compound obtained in the above reaction (B), was dissolved in 4 ml of methylene chloride and 0.8 ml of anisol, and cooled to 0° C. A solution comprising 8 ml of trifluoroacetic acid and 4 ml of methylene chloride which was preliminary cooled to 0° C., was added thereto at once, and stirred for 1 hour at the same temperature. The solvent was distilled off under reduced pressure, and ethyl ether was added to the residue to obtain 75 mg of a crude product. The crude product was suspended in 1 ml of water and adjusted to pH 7.1 with sodium hydrogencarbonate, and purified by a reversed phase column chromatography (LC Sorb RP-18, manufactured by Kemco Co.; elution with a 5% methanol aqueous solution) to obtain 44 mg (yield: 45.6%) of the above identified compound.

MP: 140° C. (decomposed):
IR(KBr)cm$^{-1}$: 1380, 1630, 1760, 3400:

NMR(D₂O) δ: 3.12 and 3.50(1H, ABq, J=18Hz), 3.16 and 3.54(1H, ABq, J=18Hz), 4.20(2H, br s), 4.95(2H, br s), 5.06(1H, d, J=4.5Hz), 5.52(1H, s), 5.61(0.5H, d, J=4.5Hz), 5.65(0.5H, d, J=4.5Hz), 6.90(0.5H, s), 6.92(0.5H, s), 7.30–7.50(5H, m), 7.75(2H, d, J=7Hz), 8.15(1H, d, J=7Hz), 8.23(1H, d, J=7Hz).

EXAMPLE 4

Preparation of 7-[2-(2-aminothiazol-4-yl)-2-(3,4-dihydroxybenzyloxyimino)acetamido]-3-(1-carboxymethylpyridinio-4-yl)thiomethyl-3-cephem-4-carboxylate (syn-isomer)

(A) 1.0 g (1.4 mmol) of 2-[3,4-di(2-methoxyethoxymethoxy)benzyloxyimino]-2-(2-tritylaminothiazol-4-yl)acetic acid (syn-isomer) and 0.56 g (1.4 mmol) of benzhydryl 7-amino-3-chloromethyl-3-cephem-4-carboxylate were dissolved in 0.77 ml (6.3 mmol) of N,N-dimethylaniline at 0° C., and 0.12 ml (1.7 mmol) of phosphorus oxychloride was dropwise added thereto. The mixture was stirred for 30 minutes and the reaction solution was washed with sequentially with 1 N hydrochloric acid, a 10% sodium hydrogencarbonate aqueous solution and a saturated sodium chloride aqueous solution. The water layer was further extracted with ethyl acetate, and the organic layer was added thereto. After drying over anhydrous sodium sulfate, the solvent was distilled off under reduced pressure to obtain benzhydryl 3-chloromethyl-7-{2-[3,4-di(2-methoxyethoxymethoxy)benzyloxyimino]-2-(2-tritylaminothiazol-4-yl)acetamido}-3-cephem-4-carboxylate (syn-isomer), which was used for the next reaction without purification.

(B) 225 mg (0.2 mmol) of the compound obtained in the above reaction (A), was dissolved in 1.8 ml of N,N-dimethylformamide, and 74 mg of (0.23 mmol) of 1-benzhydryloxycarbonylmethyl-4-pyridothione was added thereto. The mixture was stirred for 1.5 hours at room temperature. 10 ml of ethyl acetate was added to the reaction solution, and washed with 0.1 N hydrochloric acid and a saturated sodium chloride aqueous solution and dried over anhydrous sodium sulfate. The solvent was distilled off under reduced pressure, and ether was added to the residue to obtain 230 mg of benzhydryl 3-(1-benzhydryloxycarbonylmethylpyridinio-4-yl)thiomethyl-7-(2-[3,4-di(2-methoxyethoxymethoxy)benzyloxyimino]-2-(2-tritylaminothiazol-4-yl)acetamido)-3-cephem-4-carboxylate chloride (syn-isomer), which was used for the next reaction without purification.

(C) 230 mg of the compound obtained in the above reaction (B) was dissolved in 5 ml of methylene chloride and 1 ml of anisol, and cooled to 0° C. A solution comprising 10 ml of trifluoroacetic acid and 5 ml of methylene chloride which was preliminary cooled to 0° C., was added thereto at once, and the mixture was stirred for 1 hour at the same temperature. The solvent was distilled off under reduced pressure, and ethyl ether was added to the residue to obtain 120 mg of a crude product. The crude product was purified by a reversed phase column chromatography (LC Sorb, RP-18, manufactured by Kemco Co.; elution with a 30% methanol aqueous solution) to obtain 48 mg (yield: 35.7%) of the above identified compound.

MP: 155° C. (decomposed):

IR(KBr)cm⁻¹: 1380, 1640, 1765, 3450:

NMR(D₂O) δ: 3.50(2H, br s), 3.92(2H, s), 3.95(1H, d, J=5Hz), 4.45(2H, br s), 4.80(2H, br s), 5.56(1H, d, J=5Hz), 6.60–6.80(4H, m), 8.05(2H, d, J=5Hz), 8.40(2H, d, J=5Hz).

EXAMPLE 5

Preparation of 7-[2-(2-aminothiazol-4-yl)-2-(α-carboxy-3,4-dihydroxybenzyloxyimino)acetamido]-3-(1-carboxymethylpyridinio-4-yl)thiomethyl-3-cephem-4-carboxylate (syn-isomer)

(A) 4.87 g (5.19 mmol) of 2-[α-benzhydryloxycarbonyl-3,4-di(2-methoxyethoxymethoxy)benzyloxyimino]-2-(tritylaminothiazol-4-yl)acetic acid (syn-isomer) and 2.34 g (5.64 mmol) of benzhydryl 7-amino-3-chloromethyl-3-cephem-4-carboxylate were dissolved in 90 ml of methylene chloride, and 3.2 ml (25.4 mmol) of N,N-dimethylaniline and 0.63 ml (6.77 mmol) of phosphorus oxychloride were dropwise added at 0° C. The mixture was stirred for 1 hour. The reaction solution was poured into 1 N hydrochloric acid, and extracted with 1 N methylene chloride aqueous solution. The organic phase was washed with 1 N sodium hydroxide aqueous solution and a saturated sodium chloride aqueous solution. The extract was dried over anhydrous sodium sulfate and the solvent was distilled off under reduced pressure to obtain a crude benzhydryl 7-{2-[α-benzhydryloxycarbonyl-3,4-di(2-methoxyethoxymethoxy)benzyloxyimino]-2-(tritylaminothiazol-4-yl)acetamido}-3-chloromethyl-3-cephem-4-carboxylate (syn-isomer), which was used for the next reaction without purification.

NMR(DMSO-d₆) δ: 3.20(3H, s), 3.21(3H, s), 3.40(6H, m), 3.68(4H, m) 4.42(2H, m), 5.15(2H, m), 5.25(2H, m), 5.66(1H, br s), 6.74(1H, s), 6.82(1H, s), 6.95(1H, s), 7.00–7.80(38H, m).

(B) The residue obtained in the above reaction (A) was dissolved in 140 ml of acetone, and 1.68 g (11.2 mmol) of sodium iodide was added thereto and stirred for 30 minutes at room temperature. The reaction solution was poured into a 10% sodium thiosulfate aqueous solution, and extracted with ethyl acetate. The organic phase was washed with a saturated sodium chloride aqueous solution, and the extract was dried over anhydrous sodium sulfate. The solvent was distilled off under reduced pressure, and the residue thereby obtained was washed with diisopropyl ether to obtain 7.40 g [yield from Process A: 100%] of a crude benzhydryl 7-{2-[α-benzhydryloxycarbonyl-3,4-di(2-methoxyethoxymethoxy)benzyloxyimino]-2-(2-tritylaminothiazol-4-yl)acetamido}-3-iodomethyl-3-cephem-4-carboxylate (syn-isomer).

NMR(DMSO-d₆) δ: 3.20(3H, s), 3.21(3H, s), 3.42(6H, m), 3.70(4H, m) 4.40(2H, m), 5.18(3H, m), 5.26(2H, m), 5.70(1H, br s), 5.72(1H, m), 6.78(1H, s), 6.82(1H, br s), 6.94(1H, br s), 7.00–7.80(38H, m), 8.85(1H, br s), 9.62(1H, m).

(C) 138 mg (0.097 mmol) of the compound obtained in the above reaction (B) and 31.3 mg (0.097 mmol) of 1-benzhydryloxycarbonylmethyl-4-pyridothione were dissolved in 1.4 ml of N,N-dimethylformamide, and the mixture was stirred for 1 hour at room temperature. 10 ml of ethyl acetate was added thereto, and washed with 7 ml of 0.1 N hydrochloric acid and 7 ml of a saturated sodium chloride aqueous solution. The extract was dried over anhydrous sodium sulfate, and the solvent was distilled off under reduced pressure to obtain 160 mg of 7-{2-[α-benzhydryloxycarbonyl-3,4-di(2-methoxyethoxymethoxy)benzyloxyimino]-2-(2-tritylaminothiazol-4-yl)acetamido}-3-(1-benzhydryloxycarbonylmethylpyridinio-4-yl)thiomethyl-3-cephem carboxylate iodide (syn-isomer), which was used for the next reaction without purification.

(D) 160 mg of the compound obtained in the above reaction (C) was dissolved in 4 ml of methylene chloride and 0.8 ml of anisol was added thereto and cooled to 0° C. a solution comprising 4 ml of methylene chloride and 8 ml of trifluoroacetic acid which was preliminary cooled to 0° C., was added thereto at once, and stirred for 1 hour at the same temperature.

The solvent was distilled off under reduced pressure, and ethyl ether was added to the residue to obtain 100 mg of a crude product. The crude product was purified by a reversed phase column chromatography (LC Sorb, RP-18, Kemco Co.; elution with a 30% methanol aqueous solution) to obtain 30 mg (yield: 44%) of the above identified compound.

MP: 165° C. (decomposed):

IR(KBr)cm$^{-1}$: 1380, 1630, 1770:

NMR(DMSO-d$_6$) δ: 3.50(2H, br s), 4.40(2H, br s), 5.05(2H, s), 5.30(1H, d, J=4.5Hz), 5.65(1H, dd, J=4.5 and 8Hz), 6.70(1H, s), 6.85(1H, s), 7.10–7.50(5H, m), 8.00(2H, d, J=7Hz), 8.55(2H, d, J=8Hz), 9.50(1H, d, J=8Hz).

EXAMPLE 6

Preparation of disodium 7-[2-(2-aminothiazol-4-yl)-2-(α-carboxylate-3,4-diacetoxybenzyloxyimino)acetamido]-3-(1-carboxylatemethylpyridinio-4-yl)thiomethyl-3-cephem-4-carboxylate (syn-isomer)

69 mg (0.093 mmol) of disodium 7-[2-(2-aminothizolo-4-yl)-2-(a-carboxylate-3,4-dihydroxybenzyloxyimino)acetamido]-3-(1-carboxylatemethylpyridinio-4-yl)thiomethyl-3-cephem-4-carboxylate (syn-isomer) was dissolved in 2 ml of trifluoroacetic acid, and 0.5 ml of acetic anhydride was dropwise added thereto at 0° C. The mixture was stirred until the starting materials were completely disappeared by HPLC, and the solvent was distilled off under reduced pressure. Diisopropyl ether was added to the residue, and the precipitates were collected by filtration. The precipitates were adjusted to pH 6.5 with a saturated sodium hydrogencarbonate aqueous solution, and purified by a reversed phase column chromatography (LC Sorb, RP-18 manufactured by Kemco Co.; elution with a 0.5–5% methanol aqueous solution) to obtain 15 mg (yield: 19.5%) of the above identified compound.

MP: 160° C. (decomposed)

IR(KBr)cm$^{-1}$: 1380, 1630, 1760, 3400:

NMR(D$_2$O) δ: 2.00(6H, s), 3.50(2H, ABq), 4.50(2H, br s), 5.05(1H, s), 5.10(2H, s), 5.50(1H, d, J=4Hz), 5.76(1H, d, J=4Hz), 7.00–7.05(4H, m), 7.90(2H, d, J=5Hz), 8.50(2H, d, J=5Hz),

EXAMPLE 7

Preparation of sodium 7-[2-(2-aminothiazol-4-yl)-2-phenoxyiminoacetamido]-3-(1-carboxylatemethylpyridinio-4-yl)thiomethYl-3-cephem-4-carboxylate (syn-isomer)

77.7 mg (yield: 40.7%) of the above identified compound was prepared from 252 mg (3 mmol of benzhydryl 3-chloromethyl-7-[2-phenoxyimino-2-(2-tritylaminothiazol-4-yl)acetamido]-3-cephem-4-carboxylate (syn-isomer) and 97 mg (3 mmol) of 1-benzhydryloxycarbonylmethyl-4-pyridothione in the same manner as in Example 3(B) and (C).

MP: 165° C. (decomposed):

IR(KBr)cm$^{-1}$: 1380, 1520, 1640, 1765, 3430:

NMR(D$_2$O/DMSO-d$_6$) δ: 3.55(2H, ABq), 4.50(2H, br s), 4.90(2H, s), 5.13(1H, d, J=4.5Hz), 5.75(1H, d, J=4.5Hz), 7.06(1H, s), 7.30(5H, m), 7.86(2H, d, J=6Hz), 8.33(2H, d, J=6Hz).

REFERENCE EXAMPLE 1

Preparation of 2-[3,4-di(2-methoxyethoxymethoxy)benzyloxyimino]-2-(2-tritylaminothiazol-4-yl) acetic acid and sodium salt thereof (syn-isomer)

(A) 6.9 g (50 mmol) of 3,4-dihyroxybenzaldehyde was dissolved in 140 ml of methylene chloride, and 26.1 ml (150 mmol) of diisopropylethyl amine was added thereto. 17 ml (150 mmol) of 2-methoxyethoxymethyl chloride was dropwise added thereto at 0° C., and the mixture was stirred for 1 hour at 0° C. The reaction solution was sequentially washed with 50 ml of water, 0.5 N sodium hydroxide aqueous solution and 50 ml of a saturated sodium chloride aqueous solution, and the organic phase was dried over anhydrous sodium sulfate. The solvent was distilled off under reduced pressure to obtain 15.7 g (yield: 100%) of 3,4-di(2-methoxyethoxymethoxy)benzaldehyde.

NMR(CDCl$_3$) δ: 3.40(6H, s), 3.60(4H, m), 3.89(4H, m), 5.39(2H, s), 5.42(2H, s), 7.30(1H, d, J=7Hz), 7.55(1H, dd, J=1 and 7Hz), 7.70(1H, d, J=1Hz), 9.86(1H, s).

(B) 15.7 g (50 mmol) of the compound obtained in the above reaction (A) was dissolved in 300 ml of methanol, and sodium boron hydride was added several times in the total amount of 1.89 g (50 mmol) under cooling and stirred for 30 minutes. 2.86 ml of acetic acid was added to the reaction solution and stirred for 10 minutes, and the solvent was distilled off under reduced pressure The residue was dissolved in 300 ml of ethyl acetate, and the extract was washed with a saturated sodium chloride aqueous solution and dried over anhydrous sodium sulfate. The solvent was distilled off to obtain 15.0 g (yield: 98.4%) of 3,4-di(2-methoxyethoxymethoxy)benzylalcohol.

NMR(CDCl$_3$) δ:3.35(6H, s), 3.50(1H, s), 3.55(4H, m), 3.85(4H, m) 4.55(2H, s), 5.26(4H, s), 6.90(1H, dd, J=1 and 7Hz), 7.13(1H, d, J=7Hz), 7.60(1H, d, J=1Hz)

(C) 230 ml of methylene chloride was added to 12.9 g (40.8 mmol) of the compound obtained in the above reaction (B) and 16.1 g (203.7 mmol) of pyridine, and 80 ml of a methylene chloride solution including 5.8 ml (81.6 mmol) of thionyl chloride was dropwise added thereto under cooling with ice and stirred for 2 hours. The reaction solution was washed sequentially with water, a saturated sodium hydrogencarbonate aqueous solution and a saturated sodium chloride aqueous solution, and dried over anhydrous sodium sulfate. The solvent was distilled off under reduced pressure and subjected to silica gel column chromatography (ethyl acetate:hexane=1:1) to obtain 11.5 g (yield: 84.3%) of 3,4-di(2-methoxyethoxymethoxy)benzyl chloride.

NMR(DMSO-d$_6$) δ: 3.30(6H, s), 3.50(4H, m), 3.80(4H, m), 4.73(2H, s), 5.30(4H, s), 7.10–7.20(3H, m)

(D) 52 g (1.11 mol) of ethyl 2-hydroxyimino-2-(2-tritylaminothiazol-4-yl)acetate (syn-isomer) was dissolved in 520 ml of N,N-dimethylformamide, and 5.4 g (0.11 mol) of a 50% oily sodium hydride was added thereto at 0° C. The mixture was stirred for 15 minutes, and 18.8 g (0.12 mol) of sodium iodide was added. Then, a solution comprising 42 g (0.12 mol) of 3,4-di(2- methoxyethoxymethoxy)benzylchloride and 300 ml of N,N-dimethylformamide was added thereto and the mixture was stirred for 1 hour at 70° C. The solvent was distilled off under reduced pressure, and the residue was dissolved in ethyl acetate. The solution was washed sequentially with water and a saturated sodium chloride aqueous solution, and the water layer was further extracted with ethyl acetate. The organic phase was added thereto and dried over anhydrous sodium sulfate. The solvent was distilled off under reduced pressure and the residue was purified by silica gel column chromatography (ethyl acetate:n-hexane=3:1) to obtain 58 g (yield: 69%) of an oily product of 2-[3,4-di(2-methoxyethoxymethoxy)benzyloxyimino]-2-(2-tritylaminothiazol-4-yl)acetate (syn-isomer).

IR(KBr)cm$^{-1}$: 1515, 1740, 2930:

NMR(DMSO-d$_6$) δ: 1.10(3H, t, J=7Hz), 3.22(6H, s), 3,46(4H, m) 3.72(4H, m), 4.00(2H, q, J=7Hz), 5.00(2H, br s), 5.21(4H, br s), 6.90(1H, s), 7.00-7.50(18H, m), 8.75(1H, br s).

(E) 36.0 g (47.3 mmol) of the compound obtained in the above reaction (D) was suspended in 720 ml of ethanol, and 28.4 ml (56.8 mmol) of 2 N sodium hydroxide was added thereto, and heated for 1 hour with stirring under reflux. The reaction solution was allowed to cool, and the solvent was distilled off under reduced pressure. The precipitates were washed with n-hexane and dried to obtain 29.6 g (yield: 85%) of a crude sodium salt of the above identified compound.

IR(KBrcm$^{-1}$:1410, 1540, 1610, 3420:

NMR(DMSO-d$_6$) δ: 3.22(3H, s), 3.24(3H, s), 3.45(4H, m), 3.74(4H, m), 4.90(2H, br s), 5.20(4H, br s), 6.56(1H, s), 6.90-7.60(18H, m), 8.62(1H, br s).

The above mother liquor was concentrated under reduced pressure and the residue was subjected to silica gel column chromatography (10% methanol/methylene chloride) to obtain 5.3 g (yield: 15.6%) of a free acid of the above identified compound.

REFERENCE EXAMPLE 2

Preparation of 2-[α-benzhydryloxycarbonyl-3,4-di(2-(methoxyethoxymethoxy)benzyloxyimino]-2-(2-tritylaminothiazol-4-yl)acetic acid (syn-isomer)

(A) 500 ml of an aqueous solution containing 48 g (1.2 mol) of sodium hydroxide was dropwise added to a suspension of 88 g (0.8 mol) of catechol and 109.5 g (about 0.5 mol) of a 40% glyoxylic acid aqueous solution under a nitrogen atmosphere under cooling with ice, and heated to 40° C. for 5 hours. The reaction solution was adjusted to pH 2.0 with 6 N hydrochloric acid under cooling with ice, and unreacted catechol was extracted with ethyl acetate. The water layer was evaporated to dryness under reduced pressure. The residue was dissolved in 700 ml of N,N-dimethylformamide and 276 g (2 mol) of potassium carbonate, 10 g (60 mmol) of potassium iodide and 230 ml (2 mol) of benzylchloride were added thereto. The mixture was stirred for 15 hours at room temperature and further stirred for 8 hours at 40° C. The reaction solution was poured into 1.5 l of ice water and extracted with ethyl acetate, followed by washing with water and a saturated sodium chloride aqueous solution. The extract was dried over anhydrous sodium sulfate and concentrated under reduced pressure to obtain crude benzyl 3,4-dibenzyloxymandelate. 1 liter of methanol and 200 ml of an aqueous solution containing 60 g of sodium hydroxide were added to the residue and stirred for 5 hours at room temperature. The reaction solution was concentrated under reduced pressure, and 1 liter of ice water was added to the residue. The solution was adjusted to pH 2.0 with conc hydrochloric acid and extracted with ethyl acetate. The extract was dried over anhydrous sodium sulfate and concentrated under reduced pressure. The precipitated crystals were washed with isopropyl ether to obtain 83 g (yield: 45.5%) of 3,4-dibenzyloxymandelic acid.

IR(KBr)cm$^{-1}$: 735, 1030, 1095, 1140, 1235, 1270, 1425, 1520, 1705, 3500:

NMR(DMSO-d$_6$) δ: 4.95(1H, s), 5.10(4H, s), 6.99(2H, s), 7.17(1H, s), 7.40(10H, br s).

(B) 2 g (5.49 mmol) of the compound obtained in the above reaction (A) was dissolved in 20 ml of tetrahydrofuran at room temperature, and 0.50 g of a 10% palladium carbon catalyst was added thereto and subjected to catalytic hydrogenation for 1.5 hours. The catalyst was filtered off and 1.20 g (6.1 mmol) of diphenydiazomethane was added to the filtrate and the mixture was stirred for 12 hours at room temperature. The solvent was distilled off under reduced pressure and the residue was dissolved in ethyl acetate, followed by washing with a 5% of sodium hydrogencarbonate aqueous solution. The organic layer was dried over anhydrous sodium sulfate, and the solvent was distilled off under reduced pressure to obtain 1.38 g (yield: 76%) of crude benzhydryl 3,4-dihydroxymandelate, which was used to the next reaction without purification.

NMR(DMSO-d$_6$) δ: 5.09(1H, d, J=4Hz), 5.86(1H, d, J=4Hz), 6.60-6.90 (3H, m), 6.76(1H, s), 7.00-7.60(10H, m).

(C) 6.9 g (about 19.7 mmol) of the compound obtained in the above reaction (B) was dissolved in 140 ml of methylene chloride and 13.8 ml (79 mmol) of diisopropylethyl amine was added thereto and cooled to 0° C. 8.9 ml (79 mmol) of 2-methoxyethoxymethyl chloride was dropwise added thereto, and the mixture was stirred for 1 hour. The reaction solution was washed sequentially with 1 N hydrochloric acid, 1 N sodium hydroxide aqueous solution and a saturated sodium chloride aqueous solution, and dried over anhydrous sodium sulfate. The solvent was distilled under reduced pressure, and the residue was subjected to silica gel column chromatography (Wakogel C-300). The fractions containing the desired compound (ethyl acetate:-hexane=1:1) were concentrated to obtain 6.0 g (yield: 58%) of benzhydryl 3,4-di(2-methoxyethoxymethoxy)-madelate.

NMR(DMSO-d$_6$) δ: 3.22(6H, s), 3.45(4H, m), 3.75 (4H, m), 5.18(2H, s), 5.22(2H, s), 5.25(1H, d, J=5Hz), 6.22(1H, d, J=5Hz), 6.78(1H, s), 6.90-7.60(13H, m).

(D) 5.0 g (9.5 mmol) of the compound obtained in the above reaction (C) was dissolved in 100 ml of methylen chloride and 4.35 ml of (55.0 mmol) of pyridine was added thereto. Then, a solution comprising 1.2 ml (16.5 mmol) of thionyl chloride and 12 ml of methylene chloride was dropwise added at 0° C. and the mixture was stirred for 30 minutes. The reaction solution was poured into a 10% sodium hydrogencarbonate aqueous solution, and extracted with methylen chloride. The organic layer was dried over anhydrous sodium sulfate, and the solvent was distilled off under reduced pressure. The residue thereby obtained was subjected to silica gel column chromatography (Wakogel C-300), and the fractions containing the desired compound (ethyl acetate:hexane=1:1) was concentrated to obtain 3.35 g (yield: 65%) of benzhydryl α-chloro-[3,4-di(2-methoxyethoxymethoxy)phenyl]acetate, which was used for the next reaction immediately.

(E) 9.0 g (16.5 mmol) of the compound obtained in the above reaction (D) was dissolved in 90 ml of N,N-dimethylformamide. A solution of 3.1 g (19 mmol) of N-hydroxyphthalimide, 2.68 ml (19 mmol) of triethylamine and 31 ml of N,N-dimethylformaminde was dropwise added at 0° C., and stirred for 12 hours at room temperature. Then, the reaction solution was poured into a 10% sodium hydrogencarbonate aqueous solution, and extracted with ethyl acetate 3 times, followed by washing with a saturated sodium chloride aqueous solution. After the organic layer was dried over anhydrous sodium sulfate, the solvent was distilled off under reduced pressure. The residue was subjected to silica gel column chromatography, and the fractions containing the desired product (ethyl acetate:hexane =3:1) was concentrated to obtain 9.75 g (yield: 88%) of N-[α-benzhydryloxycarbonyl-3,4-di(2-methoxyethoxymethoxy)benzyloxy]phthalimide.

NMR(DMSO-d6) δ: 3.20(6H, s), 3.38(4H, m), 3.70 (4H, m), 5.15(2H, s), 5.20(2H, m), 5.95(1H, s), 6.83(1H, s), 7.00–7.50(13H, m), 7.78(4H, s).

(F) 9.75 g (14.5 mmol) of the compound obtained in the above reaction (E) was dissolved 100 ml of methylene chloride, and 45 ml of methanol solution containing 3.12 ml (49 mmol) a 80% hydrazine hydrate was dropwise added at 0° C. The reaction solution was stirred for 15 minutes, and the precipitates were filtered off. The filtrate was dried over anhyrous sodium sulfate, and the solvent was distilled off under reduced pressure. The residue thereby obtained was subjected to silica gel column chromatography (Wakogel C-300). The fractions containing the desired product (ethyl acetate:hexane=1:3) was concentrated to obtain 5.1 g (yield: 65%) of o-[α-benzhydryloxycarbonyl-3,4-di(2-methoxyethoxymethoxy)benzyl]hydroxylamine.

NMR(DMSO-d6) δ: 3.20(6H, s), 3.48(4H, m), 3.72 (4H, m), 5.14(3H, s), 5.22(2H, s), 6.38(2H, br s), 6.80(1H, s), 7.00–7.50(13H, m). (G) 5.1 g (9.4 mmol) of the compound obtained in the above reaction (F) was dissolved in 50 ml of methanol, and a suspension of 3.5 g (8.5 mmol) of 2-(2-tritylaminothiazol-4-yl)glyoxylic acid and 41 ml of methanol was added thereto. After stirring for 15 minutes, white precipitates formed were filtered off, and washed with methanol, followed by drying. 4.87 g (yield: 55%) of the above identified compound was obtained.

NMR(DMSO-d6) δ: 3.20(6H, s), 3.41(4H, m), 3.72 (4H, m), 5.15(2H, br s), 5.26(2H, br s), 5.77(1H, s), 6.85(2H,s), 6.90–7.70(28H, m), 8.80(1H, br s).

REFERENCE EXAMPLE 3

Preparation of 2-(1-t-butoxycarbony-1-vinyloxyimino)-2-(2-tritylaminothiazol-4-yl-)acetic acid (syn-isomer)

6.03 g (20 mmol) of N-(1-t-butoxycarbony-1-vinyloxy)phthalimide was dissolved in a mixed solution of 200 ml of methylene chloride and 10 ml of methanol, and a solution of 1.88 ml of a 80% hydrazine hydrate and 40 ml of methanol was dropwise added thereto. After stirring for 1.5 hours at room temperature, the insoluble substances were removed by filtration. The filtrate was washed with a 8% aqueous ammonia 3 times, then with a saturated sodium hydrochloride aqueous solution, and dried over anhydrous sodium sulfate. The solvent was distilled off under reduced pressure, and the residue was dissolved in 120 ml of methanol. 7.46 g (18 mmol) of 2-(2-tritylaminothiazol-4-yl)glyoxylic acid added thereto and stirred for 3 hours at room temperature. A precipitated crystal was filtered off to obtain 7.08 g (yield: 70.9%) of the above identified compound.

IR(KBr) cm−1: 700, 1100, 1630, 1725, 2970, 3400:

NMR(DMSO-d6) δ: 1.45(9H, s), 5.20(1H, br s), 5.33 (1H, br s), 7.05(1H, s), 7.10–7.40(15H, m), 8.82(1H, br s).

REFERENCE EXAMPLE 4

Preparation of 1-benzhydryloxycarbonylmethyl-4-pyrydothione (A) 4 g (42.06 mmol) of 4-hydroxypyridine was dissolved in 80 ml of N,N-dimethylformamide, and 8.7 g (62.92 mmol) of potassium carbonate and 16.45 g (63 mmol) of benzhydryl α-chloroacetate were added thereto. After stirring for 4 hours at 60° C., 200 ml of ethyl acetate was added to the reaction solution, and washed, with water and a saturated sodium chloride aqueous solution followed by drying over anhydrous sodium sulfate and treating with active carbon. The solvent was distilled off under reduced pressure, and the crystal residue was washed with ether to obtain 9.8 g (yield: 73%) of 1-benzhydryloxycarbonylmethyl-4-pyridone.

IR(KBr) cm−1: 700, 1200, 1575, 1650, 1750:

NMR(CDCl3) δ: 4.70(2H, s), 6.90(1H, s), 6.01–7.50 (14H, m).

(B) 1.35 g (4.23 mmol) of the compound obtained in the above reaction (A) was dissolved in 27 ml of tetrahydrofuran, and 940 mg (4.23 mmol) of phosphorus pentasulfide. After stirring for 3 hours at 60° C., the solvent of the reaction solution was distilled off and 50 ml of ethyl acetate was added thereto. The solution was washed with a saturated sodium hydrogencarbonate aqueous solution and a saturated sodium chloride aqueous solution, and dried over anhydrous sodium sulfate. The solvent was distilled off under reduced pressure, the residue was subjected to silica gel column chromatography (chloroform:methanol=20:1) to obtain 730 mg (yield: 51.5%) of the above identified compound.

IR(KBr) cm−1: 700, 1120, 1190, 1220, 1470, 1620, 1750:

NMR(DMSO-d6) δ: 6.16(2H, s), 6.90(1H, s), 7.18(2H, d, J=6Hz), 7.38(10H, s), 7.57(2H, d, J=6Hz).

The compounds of the present invention are novel compounds undisclosed in literatures. They have strong antibacterial activities and a broad antibacterial spectrum against sensitive and resistant Gram-positive bacteria and Gram-negative bacteria, particularly methicillin resistant *Staphylococcus aureus* and glucose non-fermentative Gram-negative rods including *Pseudomonas aeruginosa* and excellent stability against δ-lactamase, and thus they are effective as antibacterial agents.

We claim:

1. A compound having the formula

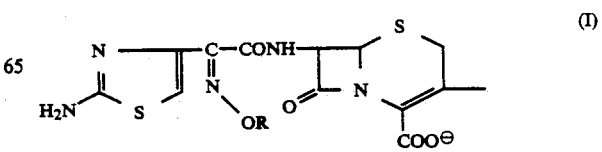

-continued

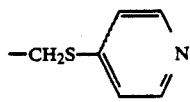

wherein R is a 1-carboxy-1-vinyl group; or a pharmaceutically acceptable salt, physiologically hydrolyzable ester or solvate thereof.

2. The compound according to claim 1, which is 7-[2-(2-aminothiazol-4-yl)-2-(1-carboxy-1-vinyloxyimino)acetamido]-3-(1-carboxymethylpyridinio-4-yl(thiomethyl-4-carboxylate.

3. An antibacterial agent comprising an antibacterially effective amount of the compound of claim 1 in admixture with a pharmaceutically acceptable carrier.

4. A method of treating an infectious disease which comprises administering an effective amount of the compound of claim 1 to a subject in need of such treatment.

5. The antibacterial agent according to claim 3 which is effective against glucose non-fermentative Gram-negative rods.

6. The antibacterial agent according to claim 3 which is effective against pseudomonads.

* * * * *